United States Patent [19]

Wu et al.

[11] 4,229,601
[45] Oct. 21, 1980

[54] CONVERTING ETHYLENE AND PROPYLENE TO THE GLYCOL USING T.BUTYL HYDROPEROXIDE IN A TWO-PHASE LIQUID REACTANT

[75] Inventors: Ching-Yong Wu, O'Hara Township, Allegheny County; Thaddeus P. Kobylinski, Gibsonia, both of Pa.

[73] Assignee: Gulf Research & Development Company, Pittsburgh, Pa.

[21] Appl. No.: 972,949

[22] Filed: Dec. 26, 1978

[51] Int. Cl.³ ............................................... C07C 31/20
[52] U.S. Cl. ..................................................... 568/860
[58] Field of Search ......................................... 568/860

[56] References Cited

U.S. PATENT DOCUMENTS

| 3,488,394 | 1/1970 | Cummins | 568/860 |
| 4,049,729 | 9/1977 | Otto et al. | 260/654 H |

FOREIGN PATENT DOCUMENTS 950669  2/1964  United Kingdom ..................... 568/860

*Primary Examiner*—Joseph E. Evans

[57] ABSTRACT

Ethylene or propylene is converted to the corresponding glycol at high selectivity in a process in which t.butyl hydroperoxide is reacted with the olefin in a two-phase liquid, organic-aqueous reaction system in the presence of osmium tetroxide and cesium, rubidium or potassium hydroxide.

11 Claims, No Drawings

CONVERTING ETHYLENE AND PROPYLENE TO THE GLYCOL USING T.BUTYL HYDROPEROXIDE IN A TWO-PHASE LIQUID REACTANT

SUMMARY OF THE INVENTION

This invention relates to a procedure for reacting ethylene or propylene with tertiary butyl hydroperoxide to produce the corresponding glycol at high selectivity.

We have discovered a process by which ethylene and propylene can be converted to the corresponding glycol at excellent overall selectivity. In our procedure a reactor containing a two-phase liquid system comprising t.butyl hydroperoxide, an organic polar solvent, an aqueous solution of cesium hydroxide, rubidium hydroxide or potassium hydroxide and osmium tetroxide is pressured with ethylene or propylene. The product mixture contains ethylene or propylene glycol with no measurable amounts of undesired oxidation by-products.

DESCRIPTION OF THE INVENTION

Ethylene glycol is currently produced commercially in a multistage process from ethylene at an overall selectivity of about 50 to 65 percent. In the first step ethylene is oxidized to ethylene oxide at elevated temperature and pressure using oxygen and a silver-containing catalyst. The reaction requires very careful control of operating conditions to obtain a selectivity as high as 70 percent. Generally, at least about one-third of the ethylene is lost as carbon dioxide. The ethylene oxide is then hydrated either catalytically using a dilute aqueous solution of a strong acid or at high temperatures and pressures, with some diethylene and triethylene glycols being formed as by-products. Other methods for producing ethylene glycol have not been commercially attractive.

Propylene glycol is currently produced commercially by several multistage processes from propylene. In these processes propylene is converted to propylene oxide. The propylene oxide is then hydrated either catalytically using a dilute aqueous solution of a strong acid or at high temperatures and pressures, with some dipropylene and tripropylene glycols being formed as by-products. No method for the direct production of propylene glycol has been commercially attractive.

U.S. Pat. No. 4,049,724 describes the direct preparation of propylene glycol from propylene in a homogeneous aqueous system using osmium tetroxide and specifying water-soluble hydroperoxides such as tertiary butyl hydroperoxide while a critical moderate pH is maintained with a suitable combination of buffering compounds.

We have surprisingly discovered that t.butyl hydroperoxide and ethylene or propylene can readily react in a two-phase, organic-aqueous system containing an organic polar solvent, an aqueous solution of the hydroxide of cesium, rubidium or potassium and osmium tetroxide to form ethylene or propylene glycol at a selectivity based on the olefin of greater than 95 percent and greater than 80 percent based on the t.butyl hydroperoxide. Furthermore, the reaction produces no measurable amounts of any oxidation by-products of ethylene or propylene. And most surprisingly, the presence of aqueous cesium or rubidium hydroxide is effective in producing the desired reaction to the glycol, while the aqueous hydroxides of sodium and lithium are essentially ineffective, with potassium hydroxide being only moderately effective.

In the present invention the reaction of t.butyl hydroperoxide with ethylene or propylene is carried out in a heterogeneous, two-phase liquid reaction. It has previously been reported in U.S. Pat. No. 4,049,724 that a homogeneous, buffered, aqueous reaction system is essential for higher concentrations of diol when tertiary butyl hydroperoxide and osmium catalyst are used. Notwithstanding this prior disclosure we have now surprisingly discovered by the present invention that a homogeneous, buffered, aqueous reaction system is not required for the reaction of t.butyl hydroperoxide with ethylene or propylene when an osmium catalyst is used. Instead, we have discovered that the selectivity of the glycol based on the t.butyl hydroperoxide is substantially greater in our novel heterogeneous, two-phase liquid reaction mixture at very high pH.

Equimolar amounts of ethylene or propylene, t.butyl hydroperoxide and water react to form equimolar amounts of t.butanol and the glycol. But some t.butyl hydroperoxide decomposes to form t.butanol and free oxygen. We believe that the novel reaction system of our invention directs the reaction to the desired glycol and minimizes the undesired decomposition of the t.butyl hydroperoxide.

The organic polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 50 and about 98 weight percent of the reaction mixture, but will preferably comprise between about 60 and about 90 percent of the reaction mixture. The preferred organic polar solvents are those which resist oxidation in the reaction system.

The amount of t.butyl hydroperoxide used in the reaction is not critical but will generally be from about one percent to about 20 weight percent of the total reaction mixture preferably from about five percent to about 20 percent of the reaction mixture. The t.butyl hydroperoxide is prepared and stored in a suitable solvent such as t.butanol which generally comprises from about 30 to about 80 weight percent t.butyl hydroperoxide. The t.butyl hydroperoxide together with this solvent is added to the reaction mixture.

Since ethylene and propylene are gases, they are incorporated into the reaction system by pressuring the reactor with the olefin. The pressure is not critical, rather it determines the amount of the olefin that is present in the reaction liquid and therefore affects the rate of reaction. We find that a pressure between about 25 and about 1,500 psig. is useful for ethylene, and a pressure of between about 5 and about 150 psig. is useful for propylene. However, we prefer to operate within a pressure range of between about 50 and about 150 psig. for ethylene and a pressure between about 10 and about 50 psig. for propylene as providing a suitable reaction rate without requiring high pressure equipment. The reaction is preferably carried out with a stoichiometric excess of the olefin to substantially completely react all of the t.butyl hydroperoxide in the reaction mixture, and more preferably at least about a 25 percent stoichiometric excess of the olefin.

The aqueous solution of the alkali metal hydroxide is critical to the success of this heterogeneous liquid reaction. We have found that cesium hydroxide and rubidium hydroxide are highly useful in our process with potassium hydroxide being only moderately effective while sodium hydroxide and lithium hydroxide are practically ineffective.

The cesium, rubidium or potassium hydroxide, or a mixture of these hydroxides, is introduced into the reaction zone as an aqueous solution. The amount of the hydroxide in the two-phase reaction mixture is not critical. As little as 0.1 weight percent of the alkali metal hydroxide based on the total reaction mixture is suitable, however, we prefer at least about 0.2 weight percent of the hydroxide. As much as about ten weight percent of the alkali metal hydroxide based on the total reaction mixture can be used, but we prefer that a maximum amount of about five weight percent of the hydroxide be used. The pH of the reaction mixture including both liquid phases will be about 14 as a result of the presence of the alkali metal hydroxide. The amount of water present in the two-phase liquid reaction mixture can be between about one and about 40 weight percent based on the total reaction mixture, and preferably can be between about two and about 20 weight percent, provided that sufficient water is used to dissolve the alkali metal hydroxide.

The catalyst, osmium tetroxide, is used in catalytic quantities. We find that from 0.01 to ten mmols of the catalyst per 100 ml. of the total reaction mixture is suitable, however, we prefer to carry out the reaction using from about 0.03 to about 0.1 mmol of catalyst per 100 ml. of the reaction mixture. The amount of catalyst can also be related to the amount of osmium metal that is used. Thus, about 50 to about 1,000 ppm. osmium can be used based on the total liquid contents of the reaction vessel, preferably about 100 to about 500 ppm. osmium. It is preferred that the osmium catalyst be added after the reactor has been pressured with the olefin since osmium catalyzes the decomposition of the hydroperoxide in the olefin's absence.

Osmium tetroxide is readily soluble in aqueous solutions of a strong base, such as alkali metal hydroxide, with which it rapidly reacts to form the perosmate, an ionic complex. Since osmium tetroxide is also soluble in many organic polar solvents, it can be dissolved in a suitable organic polar solvent for addition to the reactor where it quickly reacts with the alkali metal hydroxide forming the ionic perosmate in the aqueous solution. There must be at least a 2:1 gram atom ratio of the alkali metal to osmium metal and preferably a gram atom ratio of at least about 10:1 to provide for the perosmate complex.

We believe that in the two-phase liquid reaction mixture of our invention the osmium tetroxide functions as an oxidant in the form of the perosmate and that the osmate reduction product is oxidized back to the perosmate oxidizer by the t.butyl hydroperoxide. For this reason an alkali metal osmate or perosmate, preferably the cesium, rubidium or potassium complex that corresponds to the alkali metal hydroxide that is in the reactor, can be added directly to the reactor instead of osmium tetroxide. Therefore, in this specification including the claims reference to osmium tetroxide is intended to include the alkali metal osmates and perosmates within its scope.

The hydroxydation reaction is carried out at a moderate temperature. At higher temperatures the reaction rate increases substantially but this occurs at a significant reduction in selectivity to the glycol. At very low temperatures the selectivity to glycol is excellent but the reaction rate is slow. Within those constraints we find that a moderate reaction temperature is desirable including the range of about $-10°$ C. to about $50°$ C., but we prefer to operate within the range of about $0°$ C. to about $25°$ C.

This hydroxydation reaction can be carried out as a batch reaction, or as a semi-continuous batch reaction. In the batch reaction all the necessary components are placed in a reaction vessel and the reaction is allowed to proceed for about one to about 24 hours for substantially complete reaction of the t.butyl hydroperoxide. The reaction can be carried out in a semi-continuous manner by metering the reaction components into an agitated tank reactor, or a series of tank reactors, pressured with the olefin and removing the reaction product mixture at an appropriate rate to maintain the reactor liquid level.

The reaction product, after removal of unreacted gaseous olefin, is a two-phase mixture. It includes ethylene or propylene glycol, t.butanol, the polar solvent, the alkali metal hydroxide, an osmium compound and water. Since the reaction is generally carried out under conditions, including a stoichiometric excess of olefin for complete reaction of the t.butyl hydroperoxide, there is no significant amount of hydroperoxide in the reaction product. If unreacted t.butyl hydroperoxide shows up in the reaction product, it is removed by the use of a suitable reducing agent in an extra processing step as a safety precaution to avoid possible hazards resulting from the undesired decomposition of the hydroperoxide during product work-up. Therefore, insuring the substantial absence of t.butyl hydroperoxide in the reaction product represents a safety precaution and avoids substantial processing costs.

The reaction product is characterized by the substantial absence of oxidation products of the olefin other than the glycol corresponding to the olefin. We believe that this substantial absence of undesired oxidation by-products is, at least in part, a result of the use of a stoichiometric excess of the olefin in the reaction zone. Upon completion of the reaction, the volatile components are distilled out of the reaction mixture into various fractions including ethylene or propylene glycol. The osmium tetroxide or other osmium compounds remain in the still.

DESCRIPTION OF PREFERRED EMBODIMENTS

EXAMPLES 1-6

A series of reactions were carried out using different alkali metal hydroxides. The reactor, cooled to 0° C. in an ice-salt bath, was located in a steel safety box because of the olefin pressure that was used. The reactor was charged with 100 ml. of t.butanol, or in one experiment 100 ml. of acetone, and 7.5 ml. of a ten percent aqueous solution of the alkali metal hydroxide was introduced. After the solution had cooled to 0° C., 12 ml. of 70 percent t.butyl hydroperoxide in t.butanol (80 mmol) was added. Ethylene was pressured into the reactor to about 120 psi. followed by five ml. of 0.5 weight percent osmium tetroxide (0.1 mmol) in t.butanol which was pressured into the reactor in a stream of ethylene. Although all liquids added to the reactor were clear, two colored phases were observed in the reactor, a light yellow organic phase on top and a dark brown aqueous phase on the bottom.

The stirrer was started and the ethylene pressure was adjusted to 150 psi. This pressure and a temperature of 0° C. was maintained for six hours, at which time the reaction was near completion. In order to permit completion of the reaction, the reactor was permitted to stand at room temperature overnight. After evaporation of the solvent, the product was analyzed by gas-liquid chromatography. The yield of ethylene glycol based on the t.butyl hydroperoxide charged to the reactor is set out in the following table.

TABLE

| Example | Base | Yield, wt. % |
|---|---|---|
| 1[a] | CsOH | 80.9 |
| 2 | CsOH | 71.4 |
| 3 | RbOH | 83.0 |
| 4 | KOH | 55.0 |
| 5 | NaOH | 13.7 |
| 6 | LiOH | 5.3 |

[a]Used 100 ml. of acetone

EXAMPLE 7

In this experiment the reaction of t.butyl hydroperoxide and propylene in an aqueous, buffered system is reviewed.

A 300 ml. thick-walled glass reactor equipped with a stirring magnet was charged with 18.5 g. of water, 1.0 g. $Na_2CO_3$, 1.2 g. $NaHCO_3$ and 0.2 mmol of osmium tetroxide. A measured 26 g. portion of propylene and 15 cc. of 70 percent t.butyl hydroperoxide in t.butanol were charged into the reactor. The reaction mixture was stirred at ambient temperature (20°-25° C.) for two hours. The reaction temperature rose from 25° C. to 45° C. and then slowly dropped back to 25° C. The stirring was continued for an additional 30 minutes to insure complete reaction of the hydroperoxide. Analysis of the reaction product disclosed the production of 1.7 g. (22.4 mmols) of propylene glycol which was a selectivity of 23 percent based on the t.butyl hydroperoxide.

It is to be understood that the above disclosure is by way of specific example and that numerous modifications and variations are available to those of ordinary skill in the art without departing from the true spirit and scope of the invention.

We claim:

1. A method of preparing ethylene or propylene glycol in high yield which comprises contacting t.butyl hydroperoxide with ethylene or propylene at an elevated pressure in a heterogeneous two-phase liquid reaction system comprising an organic polar solvent, a catalytic quantity of osmium tetroxide, about 0.1 to about ten weight percent cesium hydroxide, rubidium hydroxide or potassium hydroxide and about one to about 40 weight percent water at a moderate temperature and at a pH of about 14.

2. A method of preparing ethylene or propylene glycol in high yield in accordance with claim 1 in which the temperature is between about −10° C. and about 50° C.

3. A method of preparing ethylene or propylene glycol in high yield in accordance with claim 1 in which there is between about 50 and about 98 weight percent of the organic polar solvent.

4. A method of preparing ethylene glycol in high yield in accordance with claim 1 in which the pressure of ethylene in the reaction zone is between about 25 and about 1,500 psig.

5. A method of preparing ethylene or propylene glycol in high yield in accordance with claim 1 in which there is between about one to about 20 weight percent t.butyl hydroperoxide.

6. A method of preparing ethylene or propylene glycol in high yield in accordance with claim 3 in which the polar solvent is selected from aliphatic alcohols, aliphatic ketones and aliphatic ethers having up to about six carbon atoms.

7. A method of preparing ethylene or propylene glycol in high yield in accordance with claim 2 in which there is about 50 to about 1,000 ppm. osmium as the metal based on the total reaction mixture.

8. A method of preparing propylene glycol, in high yield in accordance with claim 1 in which the pressure of propylene is between about 5 and about 150 psig.

9. A method of preparing ethylene or propylene glycol in high yield in accordance with claim 1 in which the alkali metal hydroxide is cesium hydroxide.

10. A method of preparing ethylene or propylene glycol in high yield in accordance with claim 1 in which there is between about 0.2 and about five weight percent of the alkali metal hydroxide and between about two and about 20 weight percent water based on the total liquid reaction mixture.

11. A method of preparing ethylene or propylene glycol in high yield which comprises contacting t.butyl hydroperoxide with a stoichiometric excess of ethylene under a pressure of about 50 to about 150 psig. in a two-phase liquid reaction system comprising about 60 to about 90 weight percent of an organic polar solvent based on the total reaction mixture, about 0.01 to about ten mmols of osmium tetroxide per 100 ml. of the reaction mixture, about 0.2 to about five weight percent of cesium hydroxide or rubidium hydroxide and about two to about 20 weight percent water at a temperature between about −10° C. and about 50° C. and a pH of about 14.

* * * * *